US010199202B2

(12) United States Patent
Shindo et al.

(10) Patent No.: US 10,199,202 B2
(45) Date of Patent: Feb. 5, 2019

(54) PLASMA IRRADIATION APPARATUS AND PLASMA IRRADIATION METHOD

(71) Applicant: Oral 28 Inc., Kanagawa (JP)

(72) Inventors: Toyohiko Shindo, Sagamihara (JP); Yumino Genba, Joetsu (JP); Masuji Yamaguchi, Sagamihara (JP)

(73) Assignee: Oral 28 Inc., Kanagawa (JP)

( * ) Notice: Subject to any disclaimer, the term of this patent is extended or adjusted under 35 U.S.C. 154(b) by 0 days.

(21) Appl. No.: 15/564,407

(22) PCT Filed: Apr. 9, 2015

(86) PCT No.: PCT/JP2015/061135
§ 371 (c)(1),
(2) Date: Oct. 4, 2017

(87) PCT Pub. No.: WO2016/163007
PCT Pub. Date: Oct. 13, 2016

(65) Prior Publication Data
US 2018/0138019 A1    May 17, 2018

(51) Int. Cl.
*A01C 1/00*         (2006.01)
*H01J 37/32*        (2006.01)
(Continued)

(52) U.S. Cl.
CPC .......... *H01J 37/32366* (2013.01); *A61C 5/77* (2017.02); *B01J 19/08* (2013.01);
(Continued)

(58) Field of Classification Search
CPC .. A61C 5/77; A61C 5/10; A61C 13/00; A61C 13/08; H01J 37/32366;
(Continued)

(56) References Cited

U.S. PATENT DOCUMENTS 5,236,512 A * 8/1993 Rogers .................... A47L 11/00
                                                        134/1
2004/0206365 A1* 10/2004 Knowlton .............. A61B 18/14
                                                        128/898
(Continued)

FOREIGN PATENT DOCUMENTS

JP    2003-286122 A    10/2003
JP    2008-273913 A    11/2008
(Continued)

OTHER PUBLICATIONS

Written Opinion issued in PCT/JP2015/061135; dated Jun. 2, 2015.
(Continued)

*Primary Examiner* — Nicholas Lucchesi
(74) *Attorney, Agent, or Firm* — Studebaker & Brackett PC

(57) ABSTRACT

Provided are a plasma irradiation apparatus and plasma irradiation method capable of converting a silica precursor to a high quality silica film in a short time without thermal effects on the object being processed. This plasma irradiation apparatus 1 is provided with a plasma-generating unit 12 and an irradiation unit 80 for irradiating the plasma generated by the plasma-generating unit 12 on an object to be processed, and is characterized in that irradiation unit 80 comprises a coating part 85 capable of coating a liquid on the object being processed.

6 Claims, 5 Drawing Sheets

(51) Int. Cl.
*B01J 19/08* (2006.01)
*C01B 33/12* (2006.01)
*A61C 5/77* (2017.01)
*H05H 1/24* (2006.01)
*H05H 1/42* (2006.01)

(52) U.S. Cl.
CPC ............ *B01J 19/088* (2013.01); *C01B 33/12* (2013.01); *H01J 37/3244* (2013.01); *H01J 37/32807* (2013.01); *H05H 1/2406* (2013.01); *H05H 1/42* (2013.01); *B01J 2219/0879* (2013.01); *B01J 2219/0894* (2013.01); *H01J 2237/332* (2013.01); *H05H 2001/2456* (2013.01); *H05H 2245/122* (2013.01); *H05H 2245/125* (2013.01); *H05H 2277/10* (2013.01)

(58) Field of Classification Search
CPC ............ H01J 37/3244; H01J 37/32807; H01J 2237/332; B01J 19/088; B01J 2219/0879; B01J 2219/0894; C01B 33/12
See application file for complete search history.

(56) References Cited

U.S. PATENT DOCUMENTS

| | | | | |
|---|---|---|---|---|
| 2008/0006954 | A1* | 1/2008 | Yubuta | B01J 19/088 264/5 |
| 2008/0075649 | A1* | 3/2008 | Hung | B01J 19/088 423/335 |
| 2010/0028561 | A1 | 2/2010 | Dubreuil et al. | |
| 2013/0068732 | A1* | 3/2013 | Watson | A61M 16/12 219/121.5 |
| 2014/0099597 | A1* | 4/2014 | Bergheim | A61C 17/02 433/80 |
| 2015/0203650 | A1* | 7/2015 | Kolb | C01G 25/00 428/220 |
| 2015/0340207 | A1* | 11/2015 | Holbeche | A61B 18/042 156/345.33 |
| 2016/0095679 | A1* | 4/2016 | Khakpour | A61C 17/0202 433/81 |

FOREIGN PATENT DOCUMENTS

| | | |
|---|---|---|
| JP | 2010-137372 A | 6/2010 |
| JP | 2010-523814 A | 7/2010 |
| JP | 5069582 A | 11/2012 |
| JP | 2014-240462 A | 12/2014 |
| WO | 2004/064129 A1 | 7/2004 |
| WO | WO 2005110626 A2 * 11/2005 | ............ B05D 1/62 |
| WO | 2010/146438 A1 | 12/2010 |
| WO | 2015/019240 A1 | 2/2015 |

OTHER PUBLICATIONS

International Search Report issued in PCT/JP2015/061135; dated Jun. 2, 2015.

The supplementary European search report issued by the European Patent Office on Feb. 7, 2018, which corresponds to European Patent Application No. 15888499.9-1211 and is related to U.S. Appl. No. 15/564,407.

* cited by examiner

PLASMA IRRADIATION APPARATUS AND PLASMA IRRADIATION METHOD

TECHNICAL FIELD

The present invention relates to a plasma irradiation apparatus and a plasma irradiation method.

BACKGROUND ART

Silica films are resistant to staining. Accordingly, there is a technology (see Patent Document 1) in which a coating liquid containing a polysilazane is coated onto a denture or the like and left in the air, the polysilazane reacts with moisture in the air, and a silica film is formed.

However, in the method recited in Patent Document 1, the speed of reaction is slow and it takes time to form (convert to) the silica film. Moreover, film properties of a silica film formed by reaction with moisture in the air are such that density is poor and the silica film is susceptible to damage.

Accordingly, there is a technology (see Patent Document 2) in which, when a polysilazane is being converted to a silica film, hydrogen peroxide is heated and vaporized and the vapor is blown onto a denture coated with the polysilazane, with the objective of making the reaction faster and improving product quality.

After the polysilazane is coated onto the denture, the base material is exposed to the high-temperature vapor containing hydrogen peroxide. As a result, the reaction converting the polysilazane to silica is accelerated by radicals produced from the hydrogen peroxide, and a uniform silica film is formed in a short time.

However, because the technology recited in Patent Document 2 employs high-temperature hydrogen peroxide, it is unsuitable for forming a silica film on a tooth in the mouth of a dental patient or the like.

A plasma can also be used in the conversion of a polysilazane to a silica film (see Patent Document 3). Plasma irradiation may shorten the duration of the conversion of the polysilazane to silica film without bringing the object being processed to a high temperature.

Patent Document 1: Japanese Unexamined Patent Application, Publication No. 2003-286122
Patent Document 2: Japanese Unexamined Patent Application, Publication No. 2008-273913
Patent Document 3: Japanese Patent No. 5069582

DISCLOSURE OF THE INVENTION

Problems to be Solved by the Invention

However, although plasma irradiation shortens the duration for conversion of a polysilazane to a silica film, when a silica film is formed on a tooth in a mouth, it is desired that the silica film be of high quality.

The present invention has been made in consideration of the circumstances described above; an object of the present invention is to provide a plasma irradiation apparatus and a plasma irradiation method that are capable of converting a silica precursor, such as a polysilazane or the like, to a high quality silica film in a short time without thermal effects on an object being processed.

Means for Solving the Problems

The present invention solves this problem with the solution described below.

According to an aspect of the present invention, a plasma irradiation apparatus is provided that includes: a plasma-generating unit; and an irradiation unit that irradiates plasma generated by the plasma generating unit at an object being processed, wherein the irradiation unit includes a coating part capable of coating a liquid onto the object being processed.

In the plasma irradiation apparatus described above, the irradiation unit may include a first tube-shaped member through which the plasma generated by the plasma-generating unit is delivered, and the coating part may include a ceramic conversion liquid-retaining member that is attached to a distal end of the first tube-shaped member.

The plasma irradiation apparatus described above may further include: a carrier gas supply unit that supplies a carrier gas; and a plasma delivery tube that delivers the plasma generated at the plasma generating unit to the irradiation unit together with the carrier gas supplied by the carrier gas supply unit, wherein the irradiation unit includes a tube-shaped member disposed at a distal end of the plasma delivery tube, and the irradiation unit tilts a flow path of the plasma at a predetermined angle with respect to a length direction axis of the plasma delivery tube and irradiates the plasma at the object being processed.

In the plasma irradiation apparatus described above, the irradiation unit may be attachable to and detachable from the plasma delivery tube.

In the plasma irradiation apparatus described above, the plasma delivery tube and the irradiation unit may include a tubular member with at least two coaxial tubes, the tubular member including a first tube-shaped member that forms a channel for the plasma and a second tube-shaped member provided at an outer periphery of the first tube-shaped member, and the plasma irradiation apparatus may further include a suction unit that applies suction inside a second channel provided between the first tube-shaped member and the second tube-shaped member.

In the plasma irradiation apparatus described above, the plasma delivery tube and the irradiation unit may include a tubular member with at least two coaxial tubes, the tubular member including a first tube-shaped member that forms a channel for the plasma and a third tube-shaped member provided at an outer periphery of the first tube-shaped member, and the plasma irradiation apparatus may further include a shielding gas supply unit that supplies a shielding gas to a first channel provided between the third tube-shaped member and the first tube-shaped member.

In the plasma irradiation apparatus described above, the irradiation unit may be fabricated of a transparent member.

According to another aspect of the present invention, a plasma irradiation method is provided that includes: coating a ceramic conversion-accelerating liquid onto an object being processed that has been coated with polysilazane; and, while coating the ceramic conversion-accelerating liquid, irradiating plasma at the object being processed.

Effects of the Invention

According to the present invention, a plasma irradiation apparatus and plasma irradiation method capable of converting a silica precursor to a high quality silica film in a short time without thermal effects on the object being processed may be provided.

PREFERRED MODE FOR CARRYING OUT THE INVENTION

First Embodiment

Figure 1:
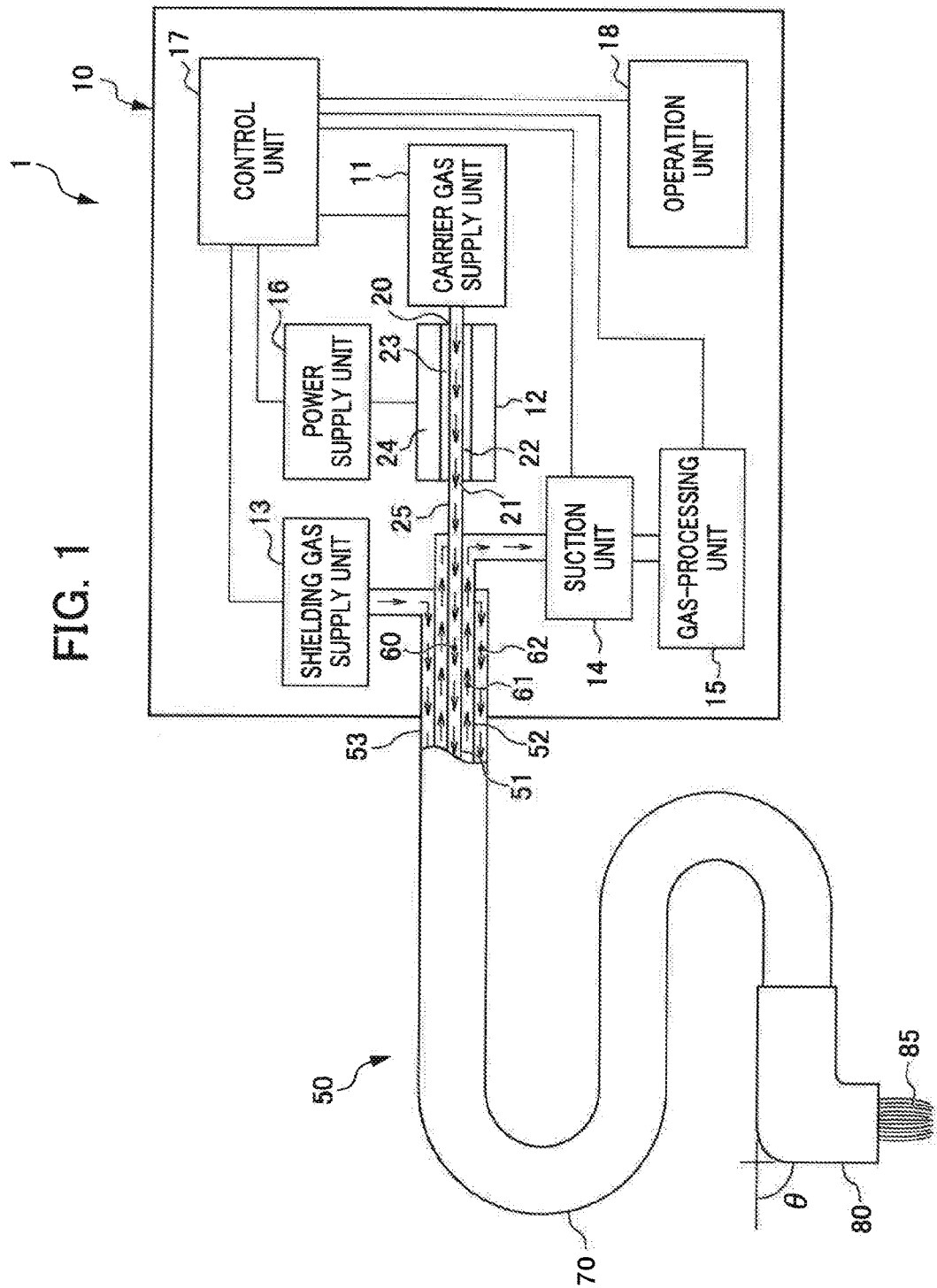
FIG. 1 is a schematic diagram of a plasma irradiation apparatus according to a first embodiment.

Below, a first embodiment of the present invention is described with reference to the attached drawings and the like. FIG. 1 is a schematic diagram of a plasma irradiation apparatus 1 according to the first embodiment. As illustrated in the drawings, the plasma irradiation apparatus 1 is equipped with an apparatus main body 10 and a plasma delivery tube 50.

(The Apparatus Main Body 10)

The apparatus main body 10 is equipped with a carrier gas supply unit 11, a plasma-generating unit 12, a shielding gas supply unit 13, a suction unit 14, a gas-processing unit 15, a power supply unit 16, a control unit 17 and an operation unit 18.

(The Carrier Gas Supply Unit 11)

The carrier gas supply unit 11 supplies a carrier gas to the plasma-generating unit 12. The carrier gas is preferably one of the noble gases, such as helium, neon, argon, krypton, xenon or the like, or nitrogen. Alternatively, the carrier gas is preferably a combination of one or two or more of these gases with oxygen, nitrogen or hydrogen. Helium facilitates extension of the plasma, so is particularly preferable.

(The Plasma-Generating Unit 12)

The plasma-generating unit 12 is equipped with a discharge tube 22, a dielectric material 23 all around an interior wall of the discharge tube 22, and two electrodes 24 disposed so as to cover the dielectric material 23. A carrier gas inlet 20 and a carrier gas outlet 21 are provided in the discharge tube 22.

In a state in which carrier gas is flowing in, the plasma-generating unit 12 applies a voltage from the power supply unit 16 between the two electrodes 24, generating atmospheric pressure plasma inside the discharge tube 22.

The carrier gas in which plasma has been generated is fed out through the carrier gas outlet 21, passes along a connecting tube 25, and is guided to the plasma delivery tube 50.

The plasma delivery tube 50 is a tubular member (pipe) with a triple coaxial tube structure, in which an inner tube (a first tube-shaped member) 51, a middle tube (a second tube-shaped member) 52 and an outer tube (a third tube-shaped member) 53 are disposed coaxially. The connecting tube 25 is coupled to the inner tube 51 of the plasma delivery tube 50. The carrier gas in which the plasma has been generated is transported along a plasma channel 60 inside the inner tube 51.

(The Suction Unit 14)

The suction unit 14 applies suction to a suction channel 61 between the inner tube 51 and middle tube 52 of the plasma delivery tube 50. As is described below, the suction unit 14 sucks in ambient gases, including the carrier gas, shielding gas and air, along the suction channel 61 from the distal end of the plasma delivery tube 50. The sucked-in ambient gases include ozone produced by a reaction between the plasma and polysilazane, which is described below.

(The Gas-Processing Unit 15)

The gas-processing unit 15 decomposes the ozone in the ambient gases including ozone that are sucked in by the suction unit 14.

(The Shielding Gas Supply Unit 13)

The shielding gas supply unit 13 supplies a shielding gas to a shielding gas channel (a first channel) 62 between the outer tube 53 and middle tube 52 of the plasma delivery tube 50.

The shielding gas is, for example, an inactive gas. A preferable shielding gas is an inactive gas such as nitrogen, argon or the like. The shielding gas prevents the dispersal of ozone, which is produced by the reaction between the plasma gas transported by the carrier gas through the inner tube 51 and the polysilazane described below.

(The Plasma Delivery Tube 50)

The plasma delivery tube 50 is a tube member with the triple coaxial tube structure described above, in which the inner tube 51, the middle tube 52 and the outer tube 53 are disposed coaxially. The plasma delivery tube 50 is provided with a delivery part 70 and an irradiation unit 80, which is attachable to and detachable from the delivery part 70.

The plasma channel 60 is formed inside the inner tube 51. An outer face of the inner tube 51 and an inner face of the middle tube 52 are retained such that a spacing therebetween is constant, forming the suction channel 61. An outer face of the middle tube 52 and an inner face of the outer tube 53 are also retained such that a spacing therebetween is constant, forming the shielding gas channel 62.

The inner tube 51, middle tube 52 and outer tube 53 are insulating bodies, and are preferably plastic, ceramic or the like. In the present embodiment, a mode is described in which cross-sectional shapes of these tubes are circular but this is not limiting; the cross-sectional shapes may be squares or the like.

(The Irradiation Unit 80)

Figure 2:
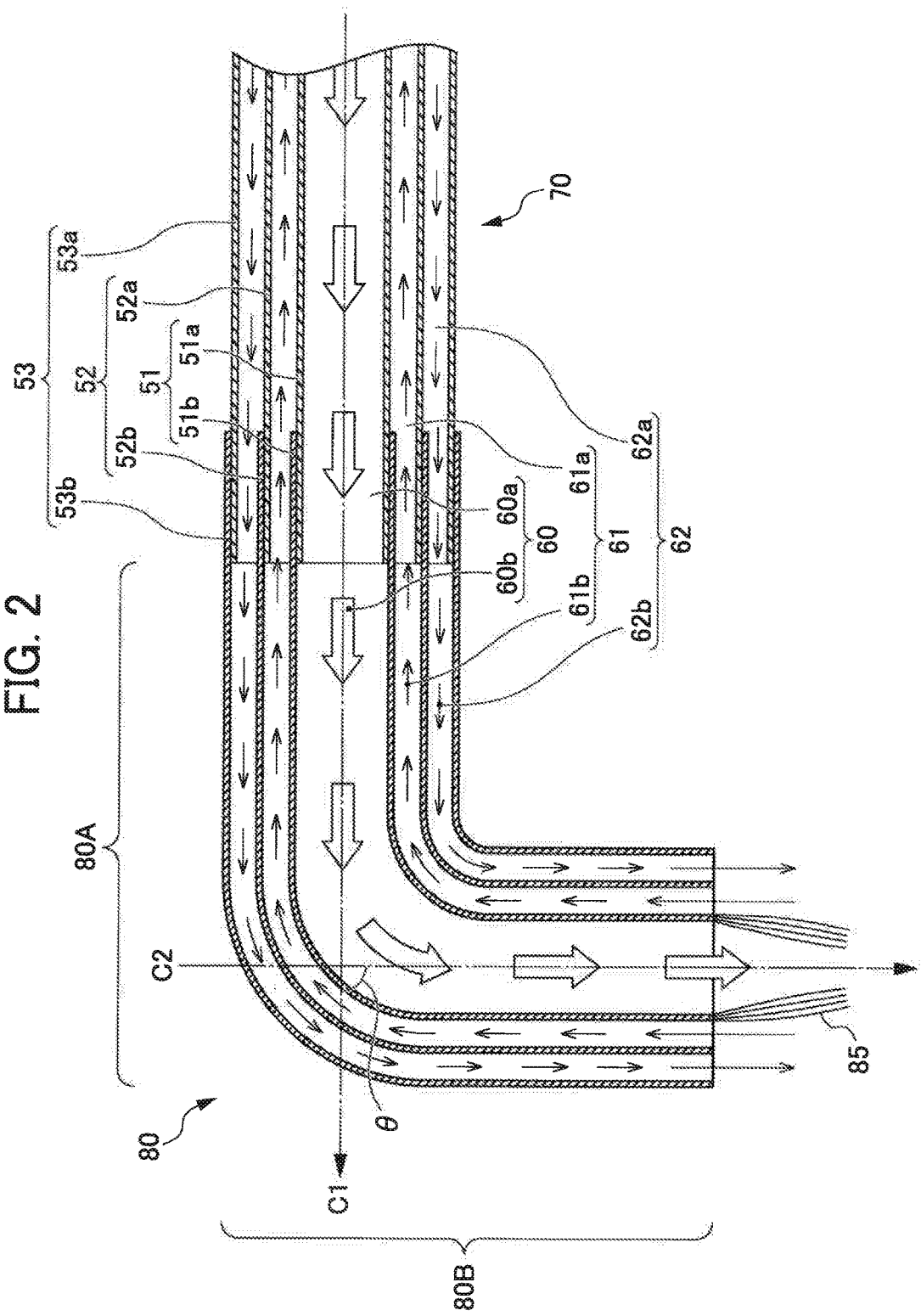
FIG. 2 is a sectional diagram of a distal end of a delivery part and an irradiation unit of a plasma delivery tube.

FIG. 2 is a sectional diagram of, of the plasma delivery tube 50, the distal end of the delivery part 70 and the irradiation unit 80.

The irradiation unit 80 includes a mounting part 80A and a distal end part 80B. The mounting part 80A is inserted into the delivery part 70. A central axis C2 of the distal end part 80B is tilted at an angle θ relative to a central axis C1 of the mounting part 80A.

An internal diameter of an inner tube 51b of the irradiation unit 80 and an external diameter of an inner tube 51a of the delivery part 70 are substantially equal; an internal diameter of a middle tube 52b of the irradiation unit 80 and an external diameter of a middle tube 52a of the delivery part 70 are substantially equal; and an internal diameter of an outer tube 53b of the irradiation unit 80 and an external diameter of an outer tube 53a of the delivery part 70 are substantially equal.

Thus, the irradiation unit 80 may be mounted to the distal end of the delivery part 70 by the central axis C1 of the mounting part 80A of the irradiation unit 80 being aligned with a central axis of the delivery part 70 and the mounting part 80A being inserted into the delivery part 70, thus tightly fitting the inner tube 51b of the irradiation unit 80 to the outer side of the inner tube 51a of the delivery part 70, tightly fitting the middle tube 52b of the irradiation unit 80 to the outer side of the middle tube 52a of the delivery part 70, and tightly fitting the outer tube 53b of the irradiation unit 80 to the outer side of the outer tube 53a of the delivery part 70.

Conversely, the mounting part 80A may be detached from the delivery part 70 by the mounting part 80A being pulled out from the delivery part 70.

In the present embodiment, the angle 9 of the distal end part 80B of the irradiation unit 80 with respect to the mounting part 80A is approximately 90°. This angle is not limited to 90°, but is preferably in a range from 0° to 120°, and more preferably in a range from 30° to 90°.

A diameter of the distal end part 80B of the irradiation unit 80 is from 1 mm to 30 mm, and is preferably from 3 mm to 15 mm.

The irradiation unit 80 is preferably a transparent member capable of blocking ultraviolet light (a glass, a resin or the like).

A brush 85 that serves as a coating part is attached to an end portion of the inner tube 51b of the distal end part 80B. In the present embodiment, the brush 85 is attached substantially uniformly along the whole of the circumference of the end portion of the inner tube 51b. The brush 85 is attached so as not to be parallel with the central axis C2 of the distal end part 80B but angled a little to the inside.

In the present embodiment, a mode is described in which the brush 85 is attached to the end portion of the inner tube 51b, but this is not limiting. For example, an alternative ceramic conversion-accelerating liquid-retaining member that is fabricated of a nonwoven fiber, textile, cotton, or porous material (sponge or the like) rather than a brush may be used, provided it is capable of absorbing hydrogen peroxide, water, alcohol or the like and coating this liquid, which is described below. The material of the coating part is preferably a plastic, bristles, natural fibers, paper, natural sponge or the like. The coating part may also be an inkjet, a spray or a roller.

Now, the plasma irradiation apparatus 1 according to the present embodiment is described in a case of use for forming a silica film on a tooth in a mouth. FIG. 3A to FIG. 3D are diagrams depicting a process that employs the plasma irradiation apparatus 1 according to the present embodiment for the coating of the silica film on the tooth in the mouth.

The present embodiment describes a mode of forming a silica film on a tooth in a mouth, but this is not limiting. The present embodiment may be employed when forming a silica film on an alternative member of, for example, a metal such as stainless steel, titanium or the like, a resin such as polycarbonate, acrylic resin or the like, a ceramic such as alumina, zirconia or the like, an accessory, a precious stone, coral, a mineral such as a fossil or the like, bone, ivory, wood, paper, leather, a silicon wafer, or the like. In the present embodiment, the object being processed is not brought to a high temperature. Therefore, the present embodiment is excellent for, for example, resins and the like that must not be brought to high temperatures.

(Polysilazane Film Forming Step)

Figure 3A:
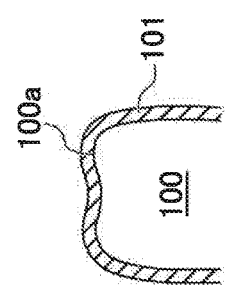
FIG. 3A is a diagram depicting a process that employs the plasma irradiation apparatus according to the first embodiment for coating of a tooth in a mouth.

As illustrated in FIG. 3A, first, a coating liquid containing polysilazane and a solvent is coated onto a tooth surface 100a of a tooth 100. The solvent is dried off and a polysilazane film 101 is formed on the tooth surface 100a.

Polysilazanes are compounds containing the coupling "—(SiH$_2$—NH)—" (in which one, some or all of the hydrogen atoms may be substituted with substituents). As examples, chain polysilazanes, ring polysilazanes and the like can be mentioned.

Chain polysilazanes that can be mentioned include perhydropolysilazane, polymethylhydropolysilazane, poly N-methylsilazane, poly N-(triethylsilyl)arylsilazane, poly N-(dimethylamino)cyclohexylsilazane, phenylpolysilazane and so forth.

One type or two more types of polysilazane may be included in the coating liquid. Perhydropolysilazane is preferable in regard to being easy to obtain and having excellent effects in forming dense silica films.

The use of a polysilazane is not a limitation; an alternative ceramic precursor may be used. For example, an alumina precursor, polysiloxane or the like may be used.

In a case of use on the tooth surface 100a, a solvent that is not harmful to the human body is to be used. For other applications, it is sufficient that the solvent does not react with the polysilazane and can form a uniform polysilazane solution.

Examples that can be mentioned include aromatic hydrocarbons such as benzene, toluene, xylene, ethylbenzene and so forth; aliphatic hydrocarbons such as pentane, hexane, isohexane, methylpentane, heptane, isoheptane, octane, isooctane and so forth; alicyclic hydrocarbons such as cyclopentane, methylcyclopentane, cyclohexane, methylcyclohexane and so forth; halogenated hydrocarbons such as methylene chloride, chloroform, carbon tetrachloride, bromoform, ethylene chloride, ethylidene chloride, trichloroethane and so forth; ethers such as methylether, isopropylether, ethylbutylether, butylether, 1,2-dioxyethane, dioxane, dimethyldioxane, tetrahydrofuran, tetrahydropyran and so forth; and the like. One type or two or more types of these solvents may be used.

The polysilazane concentration in the coating liquid is preferably from 0.01 to 50% by weight, and more preferably from 1 to 20% by weight.

A catalyst may be added to the coating liquid. Catalysts that can be mentioned include amines such as triethylamine, diethylamine, monoethanolamine, diethanolamine, n-butylamine, di-n-butylamine, tri-n-butylamine and so forth; metal hydroxides such as sodium hydroxide, potassium hydroxide and so forth; bases such as aqueous ammonia, pyridine and so forth; carboxylic acids such as acetic acid, acetic anyhydride, oxalic acid, fumaric acid, maleic acid, maleic anyhydride and succinic acid, and acidic anhydrides thereof; organic acids such as trichloroacetic acid and so forth; inorganic acids such as hydrochloric acid, nitric acid, sulfuric acid and so forth; Lewis acids such as iron trichloride, aluminium trichloride and so forth; metals such as silver, palladium, platinum, nickel, titanium, rhodium, cobalt, iron, ruthenium, osmium, iridium, aluminium and so forth, and carboxylic acids thereof; and the like.

Furthermore, appropriate additives may be included in the coating liquid in accordance with objectives, within a scope that does not interfere with the effects of the present embodiment. Additives that can be mentioned include, for example, an ultraviolet absorber, a filler constituted of a ceramic or resin, a fluoride compound, a medicinal constituent, a photocatalyst, a photosensitive component, a brightening agent and the like.

Specific additives include a calcium compound for a bioactive film; zinc oxide, silver or the like for an antibacterial action; titanium dioxide, zinc oxide or the like for ultraviolet shielding; molybdenum disulfide, tungsten disulfide or fluoride resin powder for smoothness; a filler constituted of a resin that dissolves in the solvent for film thickening, such as polymethyl methacrylate, polystyrene or the like; and so forth. In particular, a filler mixture constituted with polymethyl methacrylate is preferable. If the filler is a solid, a state in which the filler is not completely dissolved in the solvent is acceptable, but complete dissolution is more preferable.

Before the coating of the coating liquid, polishing, washing or the like may be applied to the tooth surface 100a as required.

(Hydrogen Peroxide Impregnation Step)

Figure 3B:
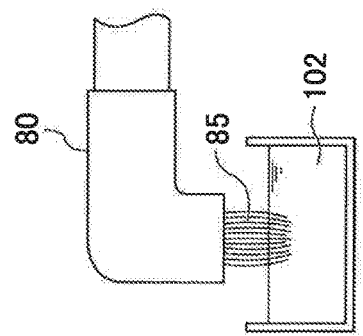
FIG. 3B is a diagram depicting a process that employs the plasma irradiation apparatus according to the first embodiment for coating of a tooth in a mouth.

Then, as illustrated in FIG. 3B, the brush 85 of the irradiation unit 80 is impregnated with aqueous hydrogen peroxide 102, which serves as the ceramic conversion-accelerating liquid.

The aqueous hydrogen peroxide 102 is water ($H_2O$) containing hydrogen peroxide ($H_2O_2$). Including a surfactant in the aqueous hydrogen peroxide 102 is preferable in regard to forming a ceramic film with excellent film characteristics.

The concentration of the aqueous hydrogen peroxide 102 is preferably 0.1 to 30% by weight, and more preferably 1 to 5% by weight. According to this concentration range, the reaction in a silica film conversion step may be made more rapid. Although the aqueous hydrogen peroxide 102 is a preferable ceramic conversion-accelerating liquid, this is not limiting; alcohol or ammonia may be used.

(Hydrogen Peroxide Coating and Plasma Irradiation Step)

Figure 3C:
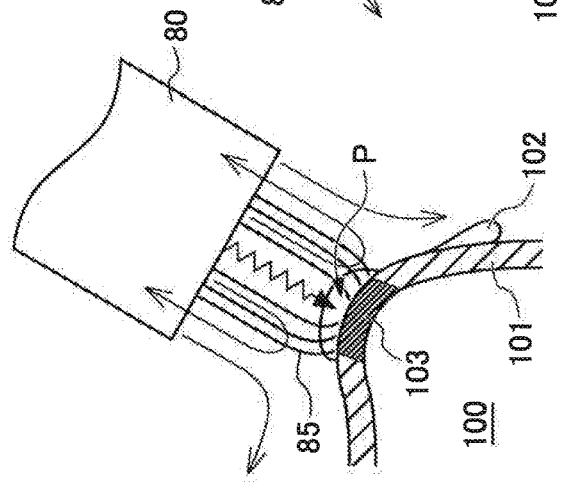
FIG. 3C is a diagram depicting a process that employs the plasma irradiation apparatus according to the first embodiment for coating of a tooth in a mouth.

As illustrated in FIG. 3C, the brush 85 into which the aqueous hydrogen peroxide 102 is impregnated coats the aqueous hydrogen peroxide 102 onto the tooth surface 100a at which the polysilazane film 101 has been formed, while the carrier gas containing the plasma that is brought through the plasma channel 60 is irradiated.

Polysilazane is thought to react with water ($H_2O$) as depicted in the following reaction formula (1) and be converted to a silica film.

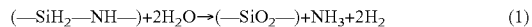

$$(-SiH_2-NH-)+2H_2O \rightarrow (-SiO_2-)+NH_3+2H_2 \quad (1)$$

When this conversion reaction takes place in an aqueous hydrogen peroxide environment, the reaction speed is accelerated and a high quality silica film 103 is formed. In the drawings, a portion of the polysilazane film 101 that has converted to the silica film 103 is shown darkened.

This is thought to be because more active radicals are produced due to radicals produced in a plasma region at atmospheric pressure reacting with the aqueous hydrogen peroxide.

According to the present embodiment, because the carrier gas is blown onto the polysilazane film 101 in the aqueous hydrogen peroxide environment, the conversion reaction is accelerated and a high quality silica film is formed.

The surface of the polysilazane film 101 is hydrophobic. Therefore, when the aqueous hydrogen peroxide 102 is coated onto the tooth surface 100a, the aqueous hydrogen peroxide 102 flows immediately.

However, according to the present embodiment, because the plasma is irradiated at the same time as the coating of the aqueous hydrogen peroxide 102 onto the tooth surface 100a, the polysilazane film 101 may be converted to the silica film 103 before the aqueous hydrogen peroxide 102 flows down off the tooth surface 100a.

Ozone may be produced by the conversion reaction. In the present embodiment, however, the surroundings of the region that is irradiated with plasma and in which the ozone is produced are subject to suction by the suction unit 14 through the suction channel 61. Therefore, the ozone is sucked up together with the carrier gas.

The sucked-up ozone is then decomposed by the gas-processing unit 15.

In the present embodiment, a shielding gas is blown out by the shielding gas channel 62 provided at the outer periphery side of the suction channel 61. Therefore, ozone gas is further prevented from flowing to the outside by the shielding gas.

The distal end part 80B of the irradiation unit 80 of the plasma irradiation apparatus 1 according to the present embodiment is tilted at 90° relative to the mounting part 80A that is inserted into the delivery part 70.

Therefore, even when the irradiation unit 80 is inserted into a narrow space such as the interior of a mouth, the direction in which the plasma is irradiated may be oriented toward the tooth 100 and it is easy to form the silica film 103 on the tooth 100.

Figure 3D:
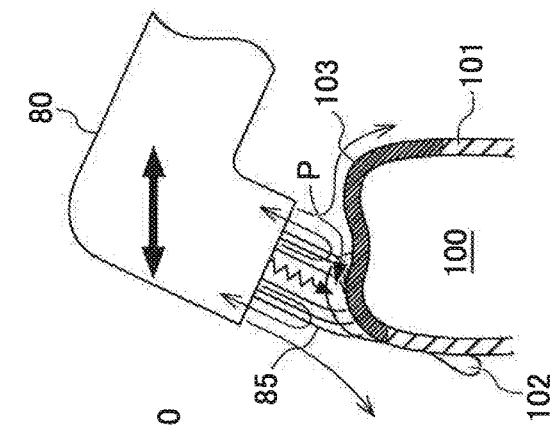
FIG. 3D is a diagram depicting a process that employs the plasma irradiation apparatus according to the first embodiment for coating of a tooth in a mouth.

When the irradiation unit 80 of the plasma irradiation apparatus 1 is moved relative to the tooth 100 as illustrated in FIG. 3D, the brush 85 and a place P at which the plasma is irradiated are moved. Therefore, the aqueous hydrogen peroxide may be coated and the plasma irradiated over a large area of the tooth surface 100a, and the high quality silica film 103 may be formed over the whole of the tooth surface 100a in a short time.

Then when, for example, plasma is to be irradiated at a tooth of a different patient, because the irradiation unit 80 is detachable from the delivery part 70, the irradiation unit 80 may be replaced. Making the irradiation unit 80 disposable contributes to hygiene.

Second Embodiment

Figure 4:
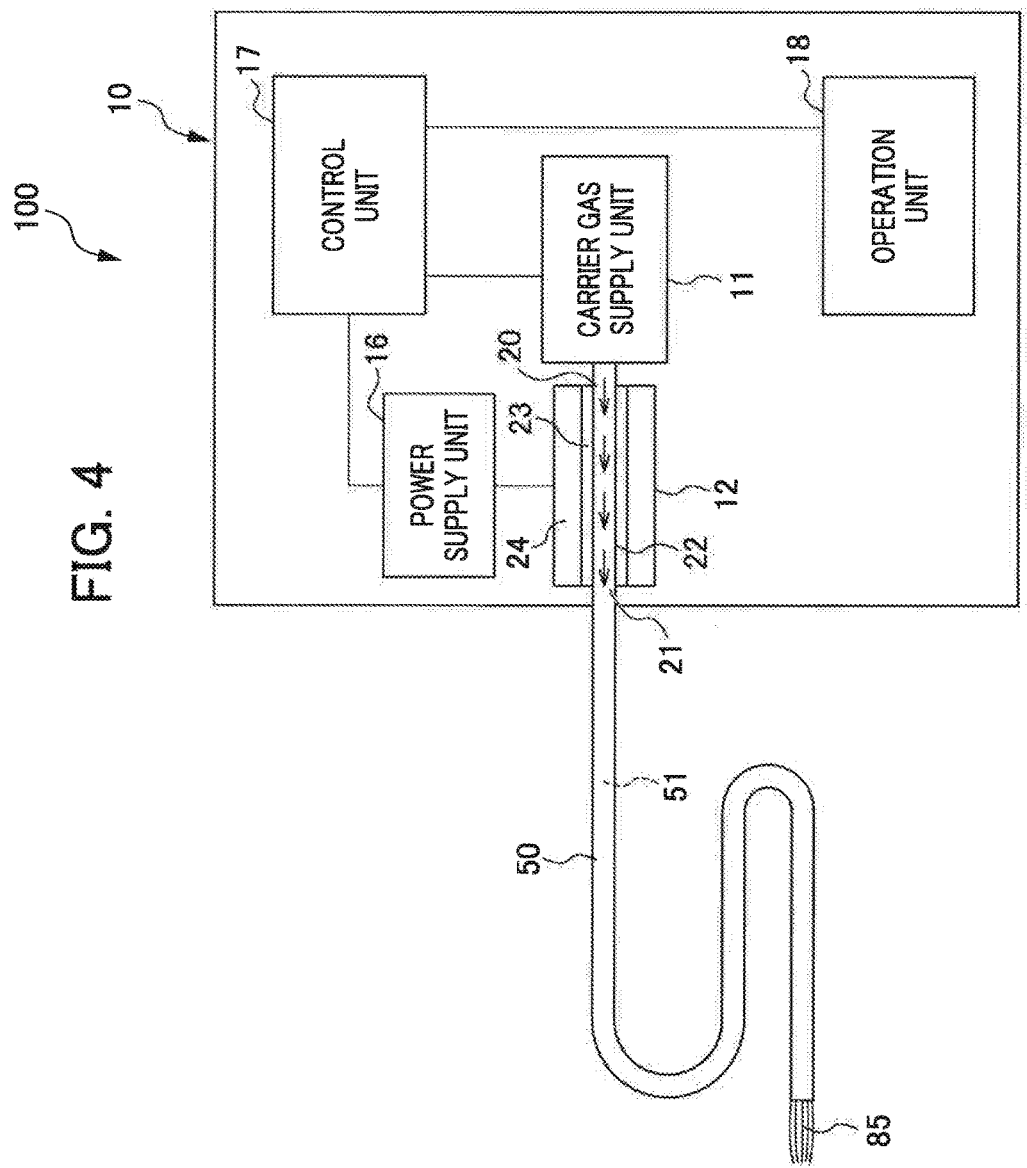
FIG. 4 is a schematic diagram of a plasma irradiation apparatus according to a second embodiment.

FIG. 4 is a schematic diagram of a plasma irradiation apparatus 200 according to a second embodiment.

Below, portions that are in common with the first embodiment are assigned the same reference symbols and descriptions thereof are not given.

The second embodiment differs from the first embodiment in that the apparatus main body 10 has a simple structure in which the shielding gas supply unit 13, the suction unit 14 and the gas-processing unit 15 are not provided. In addition, the plasma delivery tube 50 has a simple structure, being a single-wall structure that is equipped only with the inner tube 51 rather than a triple coaxial tube structure. The plasma delivery tube 50 is not divided into a delivery tube and an irradiation unit but is a single body. The distal end portion of the plasma delivery tube 50 is not curved in an "L" shape as in the first embodiment.

Because the present embodiment is not equipped with the shielding gas supply unit 13, the suction unit 14 and the gas-processing unit 15, suction is not applied to ozone that is produced. Moreover, because a shielding gas is not supplied, dispersal of ozone is not prevented. However, when plasma is being irradiated at an object for a purpose that is not, for example, forming a silica film on an actual tooth or the like, because very little ozone is produced, ozone is not a problem.

Therefore, the second embodiment is particularly suitable when forming a silica film on a material other than a tooth surface, such as, for example, a metal such as stainless steel, titanium or the like, a resin such as a polycarbonate, acrylic resin or the like, a ceramic such as alumina, zirconia or the like, an accessory, a precious stone, coral, a mineral such as a fossil or the like, bone, ivory, wood, paper, leather, a silicon wafer, and so forth.

According to the present embodiment, manufacture of the plasma irradiation apparatus 200 is simpler than in the first embodiment.

Therefore, the plasma irradiation apparatus 200 may be manufactured at lower cost. Moreover, because the plasma delivery tube 50 has a single-wall structure, the plasma delivery tube 50 may be thinner and work in small spaces is easier.

EXAMPLES

In order to verify the effects of the present embodiments, using the plasma irradiation apparatus 200 according to the second embodiment, a coating liquid containing polysilazane was coated onto a silicon wafer and dried. Then the silicon wafer was placed upright, the brush 85 was impregnated with aqueous hydrogen peroxide with a hydrogen peroxide concentration of 3%, and atmospheric pressure plasma was irradiated at the coated surface while the aqueous hydrogen peroxide was being applied to the coated surface by the brush 85.

The polysilazane that was employed was 20% NP120 (produced by AZ ELECTRONIC MATERIALS) diluted 3-fold in dibutylether.

The aqueous hydrogen peroxide with a hydrogen peroxide $H_2O_2$ concentration of 3% was used. The aqueous hydrogen peroxide was impregnated into the brush 85. The polysilazane-coated surface was irradiated with atmospheric pressure plasma for 30 seconds, 60 seconds or 120 seconds while the aqueous hydrogen peroxide was repeatedly coated onto the surface by the brush 85.

Then, transmission-type FTIR spectra of the silica film samples were measured.

Each transmission-type FTIR spectrum was measured using a Fourier transform infrared spectrophotometer (manufactured by SHIMADZU CORPORATION, product name: SHIMADZU IR Prestige-21), for a cumulative count of 50 measurements of attenuated total reflectance in a wavenumber range of approximately 4500-650 $cm^{-1}$ with a resolution of 4 $cm^{-1}$.

Figure 5:
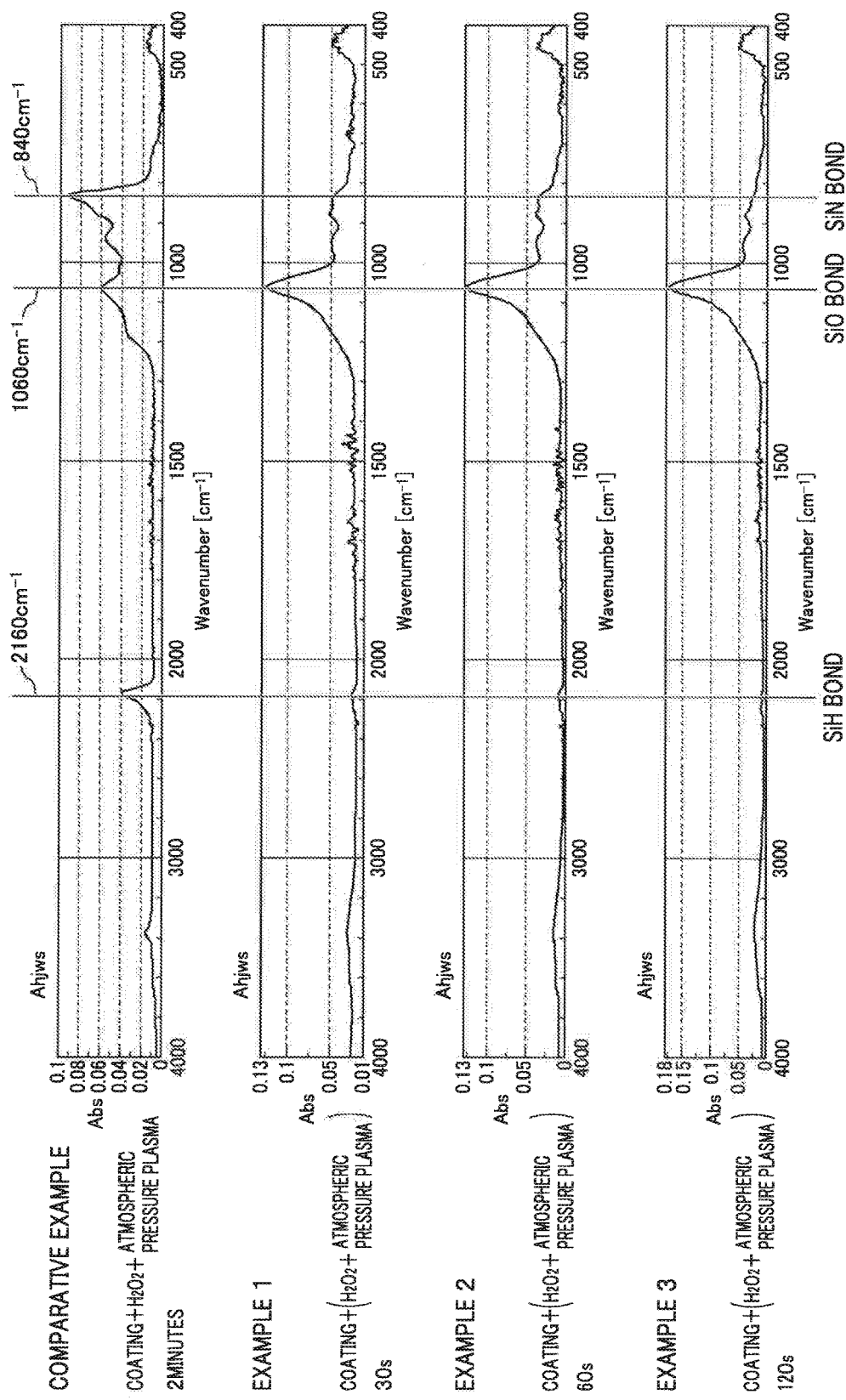
FIG. 5 is transmission-type FTIR spectra of silica film samples, depicting a Comparative Example, Example 1, Example 2, and Example 3.

FIG. 5 is transmission-type FTIR spectra of silica film samples.

FIG. 5 depicts a Comparative Example in which the coating liquid containing polysilazane is coated onto a silicon wafer and dried, after which the silicon wafer is placed upright and the aqueous hydrogen peroxide is impregnated into the brush 85. The aqueous hydrogen peroxide is applied to the coated surface by the brush 85 and, in contrast to the Examples, plasma at atmospheric pressure is irradiated for 120 seconds not at the same time but after the coating of the aqueous hydrogen peroxide.

FIG. 5 depicts Example 1, in which the coating liquid containing polysilazane is coated onto a silicon wafer that is placed upright, the aqueous hydrogen peroxide is impregnated into the brush 85, and atmospheric pressure plasma is irradiated for 30 seconds while the aqueous hydrogen peroxide is being applied to the coated surface by the brush 85.

FIG. 5 depicts Example 2, which is similar to Example 1 but the duration of coating and irradiation is 60 seconds. FIG. 5 depicts Example 3, which is similar to Example 1 but the duration of coating and irradiation is 120 seconds.

In FIG. 5, there is an absorption peak for SiO close to 1060 $cm^{-1}$, which serves as an index for silica conversion. There are also absorption peaks for SiO near 800 $cm^{-1}$ and 450 $cm^{-1}$. However, because these peaks are small, judgments are made by the 1060 $cm^{-1}$ peak.

Representing residues of unreacted polysilazane, there is an absorption peak for SiN near 840 $cm^{-1}$ and an absorption peak for SiH near 2160 $cm^{-1}$.

(a) Comparative Example

In the Comparative Example, as depicted in FIG. 5, the SiO peak near 1060 $cm^{-1}$ is barely visible, while the unreacted SiN peak near 840 $cm^{-1}$ and the unreacted SiH peak near 2160 $cm^{-1}$ are very clear.

An area coated with polysilazane is hydrophobic. Therefore, when the aqueous hydrogen peroxide is coated onto the silicon wafer that is placed upright, the aqueous hydrogen peroxide does not remain on the side face of the silicon wafer but immediately flows downward. In the Comparative Example, it is thought that, because the coating of the aqueous hydrogen peroxide and the plasma irradiation are not simultaneous, even though the plasma is irradiated at the silicon wafer, the aqueous hydrogen peroxide has already flowed down off the surface and the plasma irradiation cannot accelerate the conversion to silica.

(b) Example 1

In Example 1, as depicted in FIG. 5, the SiO peak near 1060 $cm^{-1}$ is clearly apparent.

However, the unreacted SiN peak at 840 $cm^{-1}$ and the unreacted SiH peak at 2160 $cm^{-1}$ can be seen to some extent. Therefore, a portion of the polysilazane remains unreacted.

The results for Example 1 indicate that the conversion to silica was accelerated compared to the Comparative Example. This is thought to be because, although the area coated with polysilazane is hydrophobic, in the present Example the plasma is irradiated at the same time as the coating of the aqueous hydrogen peroxide onto the silicon wafer. Therefore, the plasma is irradiated in a state in which the aqueous hydrogen peroxide is still present on the surface, and the aqueous hydrogen peroxide may accelerate the conversion to silica.

(c) Example 2

In Example 2, as depicted in FIG. 5, the SiO peak near 1060 $cm^{-1}$ appears larger than in Example 1. The unreacted SiN peak near 840 $cm^{-1}$ and the unreacted SiH peak near 2160 $cm^{-1}$ are smaller than in Example 1.

This is thought to be because the coating and irradiation duration in Example 2 is 60 seconds, which is longer than the 30 seconds of Example 1. Therefore, more of the polysilazane film is converted to the silica film than in Example 1.

(d) Example 3

In Example 3, as depicted in FIG. 5, the SiO peak at 1060 $cm^{-1}$ appears larger than in Example 1, similarly to Example 2.

The unreacted SiN peak at 840 $cm^{-1}$ and the unreacted SiH peak near 2160 $cm^{-1}$ are even smaller than in Example 2 and are almost eliminated. This is thought to be because the coating and irradiation duration in Example 3 is 120 seconds, which is longer than the 30 seconds of Example 1 and the 60 seconds of Example 2.

Therefore, more of the polysilazane film is converted to the silica film than in Example 1 and Example 2.

Effects of Embodiments (1) According to the embodiments described above, the plasma irradiation apparatus 1 is equipped with the plasma-generating unit 12 and with the irradiation unit 80 that irradiates plasma generated by the plasma-generating unit 12 at the object being processed 100; the irradiation unit 80 includes the brush 85 that is capable of coating a liquid onto the object being processed 100.

Thus, because the irradiation unit 80 that irradiates the plasma includes the brush 85 that is capable of coating the liquid onto the object being processed 100, when the plasma irradiation apparatus 1 according to the present embodiment is employed, the plasma may be irradiated while aqueous hydrogen peroxide is being coated onto the object being processed 100 at which a polysilazane film has been formed.

Therefore, the speed of conversion of the polysilazane to the silica film 103 may be accelerated and the silica film 103 may be formed with high quality.

(2) The irradiation unit 80 of the plasma irradiation apparatus 1 is equipped with the inner tube 51 through which the plasma generated by the plasma-generating unit 12 is delivered, and distal ends of the brush 85 extend toward the center of the inner tube 51.

Therefore, because the aqueous hydrogen peroxide may be coated onto a place P at which the plasma is irradiated, the speed of conversion of the polysilazane to the silica film 103 may be accelerated and the silica film 103 may be formed with high quality.

(3) The carrier gas supply unit 11 that supplies the carrier gas and the plasma delivery tube 50 that delivers the plasma generated at the plasma-generating unit 12 to the irradiation unit 80 together with the carrier gas supplied by the carrier gas supply unit 11 are provided. The irradiation unit 80 is a tube-shaped member disposed at the distal end of the plasma delivery tube 50. The irradiation unit 80 tilts the flow path of the plasma at the predetermined angle θ with respect to the length direction axis of the plasma delivery tube 50 and irradiates the plasma at the object being processed 100.

Therefore, when the irradiation unit 80 is inserted into a mouth or the like, a direction in which the plasma is irradiated may be oriented toward the tooth 100. Thus, it is easy to form the silica film 103 on the tooth 100.

(4) The irradiation unit 80 is detachable from the plasma delivery tube 50. When the plasma irradiation is applied to the tooth 100 in a mouth, because the irradiation unit 80 is detachable from the delivery part 70, the irradiation unit 80 may be discarded between one patient and the next, which is hygienic. Further, the ceramic conversion-accelerating liquid-retaining member alone may be made detachable.

(5) The plasma delivery tube 50 and the irradiation unit 80 include a tube-shaped member with at least two coaxial tubes, including the inner tube 51 that forms the plasma channel and the outer tube 53 provided at the outer periphery of the inner tube 51. The plasma irradiation apparatus is equipped with the shielding gas channel 62 provided between the outer tube 53 and the inner tube 51, and the shielding gas supply unit 13 that supplies the shielding gas.

Because the shielding gas may be jetted out by the shielding gas channel 62, flows of ozone gas to the outside may be further prevented by the shielding gas.

(6) The plasma delivery tube 50 and the irradiation unit 80 include a tube-shaped member with at least two coaxial tubes, including the inner tube 51 that forms the plasma channel and the middle tube 52 provided at the outer periphery of the inner tube 51. The plasma irradiation apparatus is equipped with the suction unit 14 that applies suction to the suction channel 61 provided between the inner tube 51 and the middle tube 52.

For example, ozone may be produced by the conversion reaction. In the present embodiment, suction is applied through the suction channel 61 by the suction unit 14 to the surroundings of an ozone production region at which the plasma is irradiated. Therefore, the ozone is sucked up together with the carrier gas.

(7) The irradiation unit 80 is fabricated of a transparent member. Therefore, for example, when plasma is being irradiated at the tooth 100 while aqueous hydrogen peroxide is being coated onto the tooth 100, because the irradiation unit 80 is transparent, a region being processed is visible and work is easier.

EXPLANATION OF REFERENCE NUMERALS

1, 200: Plasma irradiation apparatus, 10: Apparatus main body, 11: Carrier gas supply unit, 12: Plasma-generating unit, 13: Shielding gas supply unit, 14: Suction unit, 15: Gas-processing unit, 16: Power supply unit, 17: Control unit, 18: Operation unit, 50: Plasma delivery tube (tubular member), 51: Inner tube (first tube-shaped member), 52: Middle tube (second tube-shaped member), 53: Outer tube (third tube-shaped member), 60: Plasma channel, 61: Suction channel, 62: Shielding gas channel (first channel), 70: Delivery part, 80: Irradiation unit, 80A: Mounting part, 80B: Distal end part, 85: Brush (coating part), 100: Tooth, 100a: Tooth surface, 101: Polysilazane film, 102: Aqueous hydrogen peroxide, 103: Silica film

The invention claimed is:

1. A plasma irradiation apparatus comprising:
   a plasma-generating unit; and
   an irradiation unit that irradiates plasma generated by the plasma generating unit at an object being processed,
   wherein the irradiation unit includes a coating part capable of coating a liquid onto the object being processed,
   the irradiation unit includes a part of a first tube-shaped member through which the plasma generated by the plasma-generating unit is delivered, and
   the coating part includes a ceramic conversion liquid-retaining member that is attached to a distal end of the first tube-shaped member.

2. The plasma irradiation apparatus according to claim 1, further comprising:
   a carrier gas supply unit that supplies a carrier gas; and
   a delivery part that delivers the plasma generated at the plasma generating unit to the irradiation unit together with the carrier gas supplied by the carrier gas supply unit,
   wherein the irradiation unit is disposed at a distal end of the delivery part, and
   the irradiation unit tilts a flow path of the plasma at a predetermined angle with respect to a length direction axis of the delivery part and irradiates the plasma at the object being processed.

3. The plasma irradiation apparatus according to claim 2, wherein
   the irradiation unit is attachable to and detachable from the delivery part.

4. The plasma irradiation apparatus according to claim 2, further comprising:
   a second tube-shaped member provided at an outer periphery of the first tube-shaped member, and
   a suction unit that applies suction inside a second channel provided between the first tube-shaped member and the second tube-shaped member.

5. The plasma irradiation apparatus according claim 2, further comprising:
   a third tube-shaped member provided at an outer periphery of the first tube-shaped member, and
   a shielding gas supply unit that supplies a shielding gas to a first channel provided between the third tube-shaped member and the first tube-shaped member.

6. The plasma irradiation apparatus according to claim 1, wherein the irradiation unit is fabricated of a transparent member.

\* \* \* \* \*